United States Patent
Park et al.

(10) Patent No.: US 9,205,425 B2
(45) Date of Patent: Dec. 8, 2015

(54) THERMAL CYCLING REACTION BLOCK AND CONTINUOUS REAL-TIME MONITORING APPARATUS USING THE SAME

(75) Inventors: Han Oh Park, Daejeon (KR); Hanee Park, Daejeon (KR); Il Kyu Choi, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 391 days.

(21) Appl. No.: 12/999,696

(22) PCT Filed: Jun. 23, 2009

(86) PCT No.: PCT/KR2009/003376
§ 371 (c)(1),
(2), (4) Date: Feb. 8, 2011

(87) PCT Pub. No.: WO2009/157695
PCT Pub. Date: Dec. 30, 2009

(65) Prior Publication Data
US 2011/0159579 A1    Jun. 30, 2011

(30) Foreign Application Priority Data

Jun. 23, 2008  (KR) .................. 10-2008-0059211
Jun. 17, 2009  (KR) .................. 10-2009-0053677

(51) Int. Cl.
*B01L 7/00* (2006.01)
*B01L 3/00* (2006.01)
*G01N 21/64* (2006.01)

(52) U.S. Cl.
CPC ............... *B01L 7/525* (2013.01); *G01N 21/64* (2013.01); *B01L 2300/0838* (2013.01); *B01L 2300/0861* (2013.01); *B01L 2300/1805* (2013.01); *G01N 2021/6467* (2013.01)

(58) Field of Classification Search
CPC .......... B01L 3/5027; B01L 7/00; B01L 7/52; B01L 2300/08; B01L 2300/18; B01L 2300/1805; B01L 2300/1827
USPC ..................... 435/288.7; 999/288.7
See application file for complete search history.

(56) References Cited

U.S. PATENT DOCUMENTS 5,270,183 A  12/1993  Corbett et al.
5,415,839 A   5/1995  Zaun et al.
5,928,907 A   7/1999  Woudenberg et al.
(Continued)

FOREIGN PATENT DOCUMENTS

| KR | 10-0593263 | 6/2006 |
| WO | 98/16313 | 4/1998 |
| WO | 03/016558 | 2/2003 |

*Primary Examiner* — Nathan Bowers
(74) *Attorney, Agent, or Firm* — Sughrue Mion, PLLC

(57) ABSTRACT

Disclosed is real-time monitoring apparatus comprising a thermal cycling reaction block having heating block which is formed of a hollow part and divided by an insulating layer, and a capillary tube through which a sample is flowed in and/or out and which is wound on the heating block so that the different temperatures are transferred and thus reaction cycle is repeatedly performed; a light source; a band pass filter; a condensing lens; a beam splitter; a reflecting mirror which is rotatably connected with a motor so as to transfer the excitation light reflected from the beam splitter to the capillary tube and reflect the fluorescence generated from the sample in the capillary tube; and a fluorescence detecting part.

25 Claims, 6 Drawing Sheets

(56) References Cited

U.S. PATENT DOCUMENTS

| | | |
|---|---|---|
| 6,033,880 A | 3/2000 | Haff et al. |
| 6,900,059 B1* | 5/2005 | Shinn et al. ................. 436/43 |
| 2002/0109100 A1* | 8/2002 | Jackson et al. ............ 250/458.1 |
| 2004/0072335 A1* | 4/2004 | Boege et al. ............... 435/287.2 |
| 2008/0117421 A1* | 5/2008 | Yamaguchi et al. .......... 356/417 |
| 2008/0145923 A1 | 6/2008 | Hahn et al. |
| 2009/0325234 A1* | 12/2009 | Gregg et al. ................ 435/91.2 |

* cited by examiner

THERMAL CYCLING REACTION BLOCK AND CONTINUOUS REAL-TIME MONITORING APPARATUS USING THE SAME

TECHNICAL FIELD

The present invention relates to a thermal cycling reaction block and a continuous real-time monitoring apparatus using it, and more particularly, to a thermal cycling reaction block which is capable of heating or cooling samples at different temperatures so as to generate a polymerase chain reaction (PCR) and allow the PCR to be monitored in real-time, and a continuous real-time monitoring apparatus using it.

BACKGROUND ART

A polymerase chain reaction (PCR) is a method of amplifying DNA by multiple synthesis of a selected region of the DNA, thereby producing a large amount of DNA by cloning a very small amount of the DNA.

Through the PCR, only a desired segment of DNA may be amplified from very large DNA like genomic DNA. The PCT generally includes denaturation, primer annealing and DNA polymerization processes.

Recently, real-time PCR is well known to those of ordinary skill in the art. The real-time PCR is a technology which allows monitoring of a reaction state in real-time by measuring an intensity of fluorescence showing the level of DNA amplification at every cycle in a status that a reaction product in a gel is not separated by electrophoresis. Therefore, in the real-time PCR, there are some advantages in that precise quantitative analysis is allowed, and it is possible to simply and rapidly perform the analysis without the electrophoresis, and also there is less risk of contamination.

A real-time PCR apparatus includes a thermal cycler for PCR and a fluorometer for detecting fluorescence of a reaction product. A conventional real-time PCR apparatus is comprised of a thermoelectric element, a thermal block for transferring heat to a reaction tube in which a sample is received, a light source for irradiating excitation light to the sample in the tube, and a light receiving part for receiving the fluorescence generated from the sample. In the conventional real-time PCR apparatus, cooling and heating cycles are repeatedly performed by using the thermoelectric element so as to react the sample, and the excitation light is irradiated to the sample using the light source and the light receiving part at every end of each cycle, and then an amount of the fluorescence generated from the sample is measured so as to display the progress of the PCR in real-time.

However, in the conventional real-time PCR apparatus, it is possible to treat a plurality of samples, but it is impossible to successively react the samples at regular time intervals, and also it is impossible to provide other samples in the reaction tube during the reaction of the sample until the reaction is completed.

To solve the above problems, there has been proposed various continuous real-time monitoring apparatuses.

In U.S. Pat. No. 6,033,880, there is disclosed a PCR apparatus using a capillary tube. According to the PCR apparatus, a heat transfer block includes four constant temperature blocks, and samples and reagents are supplied to or removed from the capillary tube using a solution supplying unit. The PCR is performed by rotating the heat transfer block and changing temperature transferred to the capillary tube using the above-mentioned apparatus. The problem in this type apparatus is that the heat transfer block should be rotated to perform the PCR, and also the reproducibility of the PCR is deteriorated since the PCR may be changed depend on a contacting level between the capillary tube and the heat transfer block.

Further, in this type apparatus, it is impossible to perform the PCR at time intervals. Furthermore, since the above apparatus can measure the progress of the reaction only after completion of the PCR, there is another problem that a user cannot check the progress of the reaction before the completion of the PCR.

To solve the above problems, there has been proposed a new PCR real-time monitoring apparatus in Korean Patent No. 593263 (titled "a high throughput device for performing continuous-flow reactions"), in which a temperature circulating unit for PCR, comprised of a capillary tube and a circular heating block, is provided.

In this apparatus, the capillary tube of 3.5 meters in length is wound 33 times on a copper block of 30 mm in diameter, which is divided into melting, annealing and extension temperature regions. When a reaction mixture flowed in the capillary tube is circulated once around the heating block formed of copper, each cycle of the PCR is performed. In this method, the capillary tube through which the PCR sample is flowed is wound on the heating block, and the capillary tube is scanned by a scanning unit having a fluorescence detector. Thus, the scanning unit is a means for irradiating light to the capillary tube wound on the heating block using a light irradiating unit and measuring an amount of fluorescence generated in the capillary tube.

According to the above-mentioned method, the light irradiating unit for irradiating light to the capillary tube wound on the heating block and a sensor for measuring the fluorescence generated from the capillary tube are installed at a moving stage, so that the scanning unit is linearly driven and the light is irradiated, in turn, to the capillary tube according to movement of the scanning unit. Then, the fluorescence generated from the capillary tube is measured, in turn, according to the movement of the scanning unit.

In the above-mentioned technology, there is disclosed the scanning unit in which a fluorescence detecting sensor and a light source for generating a light beam having a desired wavelength are moved at a constant speed above the heating block on which the capillary tube is wound. The light source and the fluorescence detecting sensor installed at the scanning are moved in an axial direction that is parallel with a central axis of the heating block on which the capillary is wound or that is cross the central axis thereof, so as to irradiate the light to the capillary tube or measure the fluorescence. Whenever perform the scanning, monitoring of the PCR is performed once, and the multiple capillary tubes are scanned upon the scanning. In order to scan the fluorescence generated from the sample in the capillary tube while the light source and the fluorescence detecting sensor installed at the moving stage are moved at a constant speed, it is necessary to provide a motor, a conveying unit like liner conveying means, a conveying guide unit, driving means for providing power the conveying unit and so on. However, since the light source including a plurality of optical lenses uses an expensive lens like an object lens and it is also necessary to precisely arrange the light source and the fluorescence detecting sensor in order to precisely control an optical path, there is a problem that a manufacturing cost of the PCR apparatus is remarkably increased. In addition, since the PCR apparatus includes the plurality of lenses, the conveying unit, the power transferring unit, the driving means and the like, this may cause increase of its size and malfunction thereof.

Therefore, there is necessity of providing a new continuous PCR real-time monitoring apparatus which solves the above-mentioned problems and has an excellent and economical real-time monitoring effect.

DISCLOSURE

Technical Problem

An object of the present invention is to provide a thermal cycling reaction block which provides a simple monitoring apparatus so as to continuously monitor a PCR (polymerase chain reaction) in real-time, and facilely detects a PCR, and enhances detecting accuracy of the apparatus.

Technical Solution

To achieve the object of the present invention, the present invention provides a thermal cycling reaction block including a doughnut-shaped heating block 10a, 10b which is formed of a hollow part 11 at a central portion thereof and divided by an insulating layer so as to respectively provide different temperatures; and a capillary tube 20 through which a sample is flowed in and/or out and which is wound on the heating block 10a, 10b at regular intervals to be passed through the hollow part 11, so that the different temperatures are transferred and thus reaction cycle is repeatedly performed.

Preferably, the heating block 10a, 10b further includes an additional heating block 13 which surrounds the outer heating block 10b, on which the capillary tube 20 is wound, so as to be coupled with an outer side of the outer heating block 10b.

Preferably, an inserting groove 12 in which a part of the capillary tube 20 is inserted is formed in an outer surface of the heating block 10a, 10b so as to increase a contacting surface area between the heating block 10a, 10b and the capillary tube 20.

Further, the present invention provides an real-time monitoring apparatus including a thermal cycling reaction block 100 according to any one of claims 1 to 3; a light source 110 for irradiating excitation light; a band pass filter 130 for passing the excitation light having only a desired wavelength irradiated from the light source 110; a first condensing lens 140 for condensing the excitation light; a beam splitter 120 which reflects the excitation light and passes fluorescence generated from a sample in a capillary tube 20; a reflecting mirror 150 which is rotatably connected with a motor 160 so as to transfer the excitation light reflected from the beam splitter 120 to the capillary tube 20 and reflect the fluorescence generated from the sample in the capillary tube 20; and a fluorescence detecting part 170 for detecting the fluorescence that is reflected by the reflecting mirror 150 and then passed through the beam splitter 120.

Preferably, the fluorescence detecting part 170 includes a fluorescence condensing lens 171 for condensing the fluorescence passing through the beam splitter 120; a fluorescence band pass filter 172 for passing the condensed fluorescence having only a desired wavelength; and a fluorescence detecting sensor 173 for detecting the fluorescence having the desired wavelength passing through the fluorescence band pass filter 172. Further, the fluorescence detecting part 170 further includes one or more fluorescence condensing lenses 171, fluorescence band pass filters 172 and fluorescence beam splitters 174 according to a wavelength region of the fluorescence.

Further, the present invention provides an real-time monitoring apparatus including a thermal cycling reaction block 100; a light source 110 for irradiating excitation light; a band pass filter 130 for passing the excitation light having only a desired wavelength irradiated from the light source 110; a first condensing lens 140 for condensing the excitation light; a beam splitter 120 which reflects the excitation light and passes fluorescence generated from a sample in a capillary tube 20; a reflecting mirror 150 which is rotatably connected with a first motor 160a so as to transfer the excitation light reflected from the beam splitter 120 to the capillary tube 20 and reflect the fluorescence generated from the sample in the capillary tube 20; a second condensing lens 141 which is positioned between the reflecting mirror 150 and the thermal cycling reaction block 100 so as to condense the excitation light reflected from the reflecting mirror 150 and the fluorescence generated from a sample in a capillary tube 20; and a fluorescence detecting part 170 for detecting the fluorescence that is reflected by the reflecting mirror 150 and then passed through the beam splitter 120.

Preferably, the fluorescence detecting part 170 includes a fluorescence condensing lens 171 for condensing the fluorescence passing through the beam splitter 120; a fluorescence band pass filter fixing part 175 which has one or more fluorescence band pass filters 172 for passing the fluorescence having different desired wavelengths from the condensed fluorescence; a second motor 160b for rotating the fluorescence band pass filter fixing part 175; and a fluorescence detecting sensor 173 for detecting the fluorescence having the desired wavelength passing through the fluorescence band pass filters 172.

Preferably, the real-time monitoring apparatus further includes a polarizer or a polarizer film 131 between the light source 110 and the first condensing lens 140 and at a fluorescence measuring part.

Preferably, the first motor 160a and/or the second motor 160b is a constant rotation motor for rotating at a constant speed.

Advantageous Effects

Unlike the conventional apparatus using the scanning unit in which the movable light source, the movable fluorescence detecting part and the plurality of expensive object lenses are precisely arranged, the continuous real-time monitoring apparatus of the present invention uses the fixed light source and fixed fluorescence detecting part so as to be controlled by only the motor without the movement of the light source and the fluorescence detecting part, so that the real-time monitoring is performed at a fixed position. Therefore, it is facile to detect the amplification of the sample, and it is possible to enhance the detecting accuracy and reduce the manufacturing cost and effort, and it is also possible to reduce the malfunction and size thereof.

DESCRIPTION OF DRAWINGS

The above and other objects, features and advantages of the present invention will become apparent from the following description of preferred embodiments given in conjunction with the accompanying drawings, in which.

DETAILED DESCRIPTION OF MAIN ELEMENTS

| | |
|---|---|
| 10: heating block | 11: hollow part |
| 12: inserting groove | 13: additional heating block |
| 20: capillary tube | 30: insulating layer |
| 100: thermal cycling reaction block | |
| 110: light source | |
| 120: beam splitter | 130: band pass filter |
| 131: polarizer or polarizer film | |
| 132: ND filter | 140, 141: first and second condensing lenses |
| 150: reflecting mirror | 160: motor |
| 170: fluorescence detecting part | |
| 171: fluorescence condensing lens | |
| 172: fluorescence band pass filter | |
| 173: fluorescence detecting sensor | |
| 174: fluorescence beam splitter | |
| 175: fluorescence band pass filter fixing part | |

[Best Mode]

Hereinafter, the embodiments of the present invention will be described in detail with reference to accompanying drawings.

Figure 1:
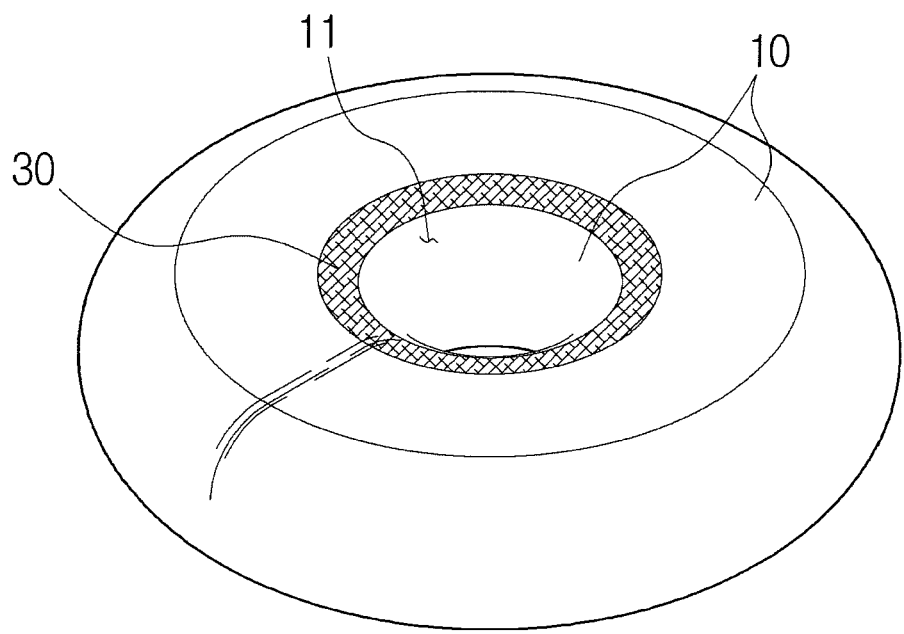
FIG. 1 is a perspective view of a heating block in accordance with an embodiment of the present invention.
Figure 2:
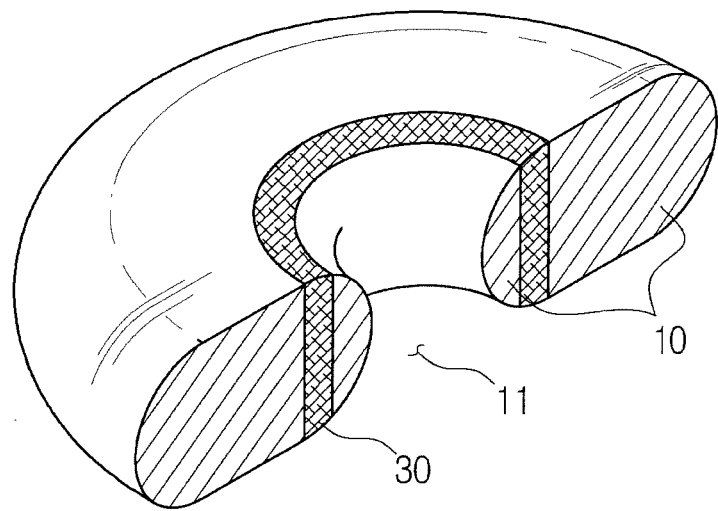
FIG. 2 is a cross-sectional perspective view of the heating block in accordance with the embodiment of the present invention.
Figure 3:
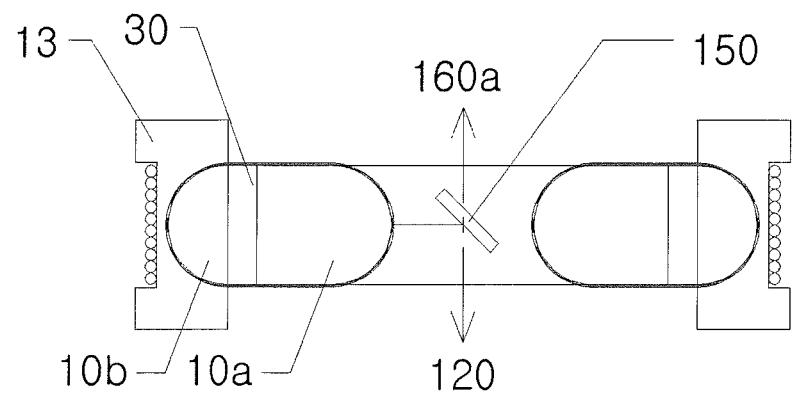
FIG. 3 is a cross-sectional view of the heating block in accordance with another embodiment of the present invention.
Figure 4:
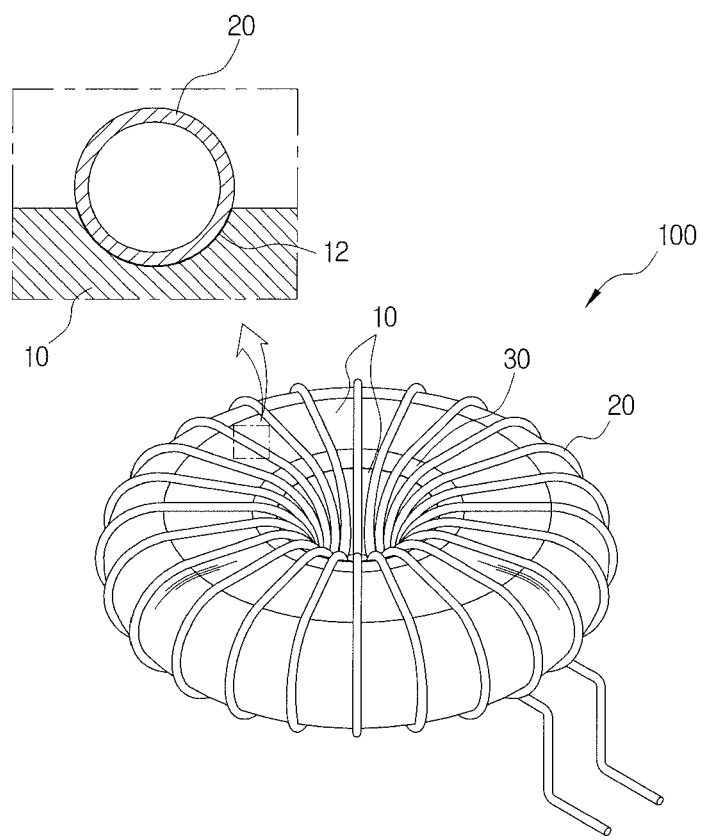
FIG. 4 is a perspective view of a thermal cycling reaction block in accordance with the embodiment of the present invention.

FIG. 1 is a perspective view of a heating block in accordance with an embodiment of the present invention, FIG. 2 is a cross-sectional perspective view of the heating block in accordance with the embodiment of the present invention, FIG. 3 is a cross-sectional view of the heat block in accordance with another embodiment of the present invention, and FIG. 4 is a perspective view of a thermal cycling reaction block in accordance with the embodiment of the present invention.

As shown in the drawings, a thermal cycling reaction block 100 has a hollow part 11 at a central portion thereof, and also includes a heating block 10a, 10b which is divided by an insulating layer so as to respectively provide different temperatures; and a capillary tube 20 through which a sample is flowed in and/or out and which is wound on the heating block 10a, 10b at regular intervals to be passed through the hollow part 11, so that the different temperatures are transferred and thus reaction cycle is repeatedly performed.

A typical polymerase chain reaction (PCR) includes a denaturation process at 94° C., an annealing process at 45~67° C., and a polymerization process at 72° C. However, even though the polymerization process is omitted, it has no problem in the PCR. Thus, a real-time PCR has a tendency to remove the reaction time of the polymerization process in order to reduce time. Although the two-divided heating block 10a, 10b is described in the drawings of the present invention, the heating block may be further divided.

At this time, since temperature interference between partitions of the heating block 10a, 10b is interrupted by the insulating layer 30, it is facile to control the temperature. The insulting layer 30 is formed of a material having a very low heat transferring rate to facilely maintain the different temperature in each partition of the heating block 10a, 10b.

In the drawings of the present invention, although the heating block 10a, 10b is formed into a long hole shape, it may have various shapes such as a circular shape, an elliptical shape, a polygonal shape and a rectangular shape.

Further, the thermal cycling reaction block 100 of the present invention may have an additional heating block 13 which surrounds the outer heating block 10b, on which the capillary tube 20 is wound, so as to be coupled with an outer side of the outer heating block 10b. This is a heat transfer method from an outer side of the outer heating block 10b to an inside direction thereof when transferring the heat to the capillary tube 20 through the additional heating block 13. Thus, the heat is further efficiently transferred to the capillary tube 20.

The sample is flowed in and/or out through the capillary tube 20. Preferably, the capillary tube 20 is passed through the hollow part 11 and spirally wound on the heating block 10a, 10b at regular intervals so that the different temperatures are transferred to each heating block 10a, 10b and thus the reaction cycle is repeatedly performed. Therefore, while the capillary tube 20 is serially and repeatedly contacted with the heating block 10a, 10b having the different temperature, the PCR is performed so as to amplify gene (DNA etc). The reason why the capillary tube 20 is wound at regular intervals is to uniformly maintain the PCR and thus to facilely rotate at a constant angle a reflecting mirror to be described later.

An inserting groove 12 in which a part of the capillary tube 20 is inserted may be formed in an outer surface of the heating block 10a, 10b so as to increase a contacting surface area between the heating block 10a, 10b and the capillary tube 20.

As shown in FIG. 4, by the spiral inserting groove 12 in which a part of the capillary tube 20 is fixedly inserted and which has a constant size and a constant interval, the contacting surface area between the heating block 10a, 10b and the capillary tube 20 is increased and thus the heat is further efficiently transferred from the heating block 10a, 10b.

Moreover, since the contacting surface area between the heating block 10a, 10b and the capillary tube 20 is associated with the reaction time of the PCR, the contacting surface area may be changed according to the reaction time condition. The reaction time may be controlled by changing a radial width of the partition of the heating block 10a, 10b. And a position of the insulating layer 30 in the heating block 10a, 10b may be also changed according to the radial width of the heating block 10a, 10b.

The thermal cycling reaction block 100 as described above is used in an real-time monitoring apparatus for measuring DNA amplification in real-time.

Figure 5:
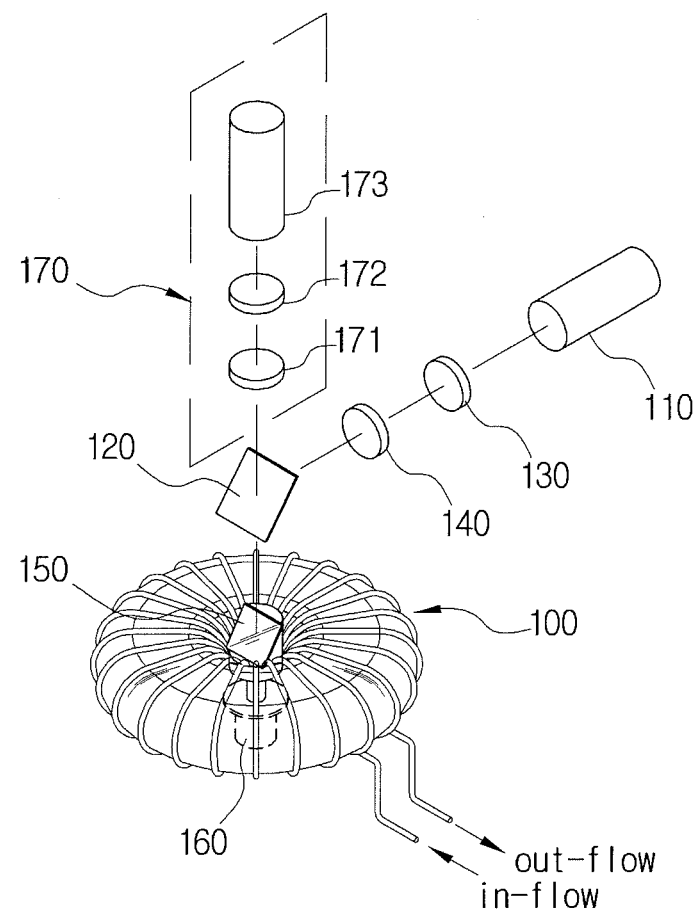
FIGS. 5 and 6 are perspective views showing a schematic structure of a real-time monitoring apparatus using the thermal cycling reaction block in accordance with an embodiment of the present invention.
Figure 6:
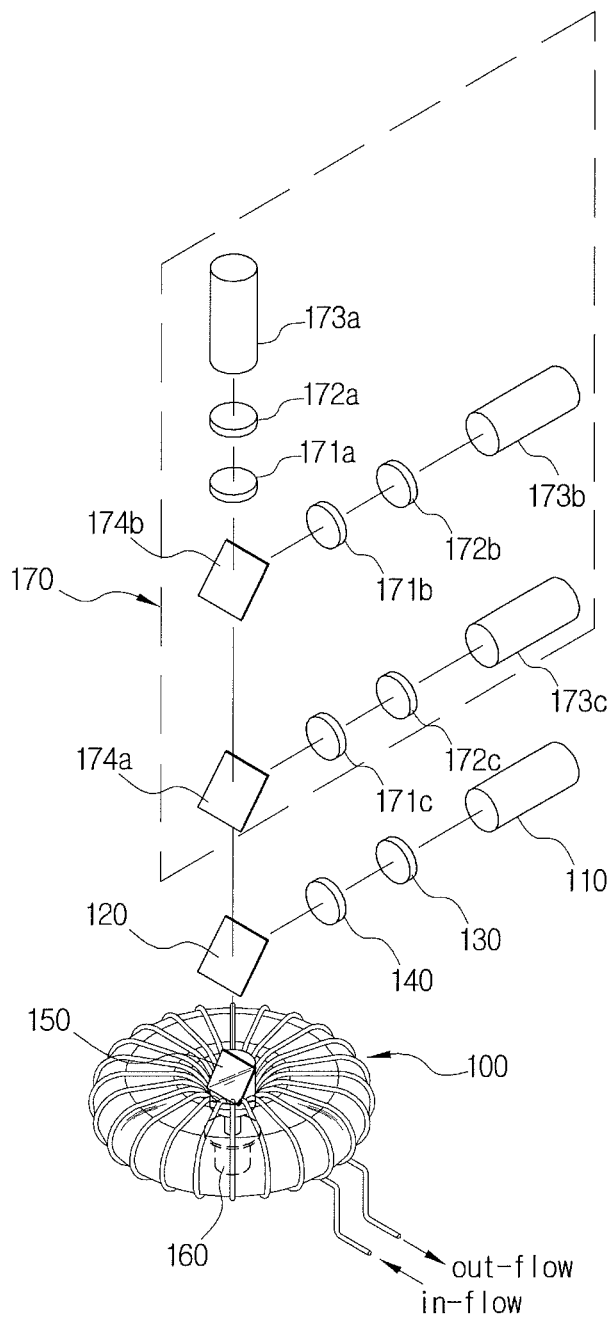

FIGS. 5 and 6 are perspective views showing a schematic structure of a real-time monitoring apparatus using the thermal cycling reaction block in accordance with an embodiment of the present invention.

As shown in the drawings, the real-time monitoring apparatus using the thermal cycling reaction block 100 in accordance with an embodiment of the present invention includes a light source 110 for irradiating excitation light; a band pass filter 130 for passing the excitation light having only a desired wavelength irradiated from the light source 110; a first condensing lens 140 for condensing the excitation light; a beam splitter 120 which reflects the excitation light and passes fluorescence generated from a sample in a capillary tube 20; a reflecting mirror 150 which is rotatably connected with a motor 160 so as to transfer the excitation light reflected from the beam splitter 120 to the capillary tube 20 and reflect the fluorescence generated from the sample in the capillary tube 20; and a fluorescence detecting part 170 for detecting the fluorescence that is reflected by the reflecting mirror 150 and then passed through the beam splitter 120.

The light source 110 functions to generate the excitation light and includes a white light source such as a tungsten halogen lamp and a xenon discharge lamp, and a single-colored light source such as LED and laser. But the light source 110 is not limited to them.

The band pass filter 130 functions to pass the excitation light having only a desired wavelength irradiated from the light source 110.

The first condensing lens 140 functions to condense the excitation light irradiated from the light source 110. The first condensing lens 140 includes any lens which condenses the excitation light, preferably, a double convex lens.

The beam splitter 120 functions to reflect the excitation light irradiated from the light source 110 and pass fluorescence generated from the sample in the capillary tube 20. Preferably, the beam splitter 120 is a dichroic beam splitter.

The excitation light reflected by the beam splitter 120 is transferred to the reflecting mirror 150, and the fluorescence passing through the beam splitter 120 is transferred to the fluorescence detecting part 170.

The reflecting mirror 150 that the excitation light reflected by the beam splitter 120 is transferred is disposed at the hollow part 11 of the thermal cycling reaction block 100. The reflecting mirror 150 functions to transfer the excitation light reflected from the beam splitter 120 to the capillary tube 20 that is spirally wound in the thermal cycling reaction block 100 and also functions to reflect the fluorescence generated from the sample in the capillary tube 20 to the beam splitter 120. The fluorescence reflected from the reflecting mirror 150 is passed through the beam splitter 120 and then transferred to the fluorescence detecting part 170. The reflecting mirror 150 is connected with the motor 160 for rotating the reflecting mirror 150. The motor 160 functions to rotate the reflecting mirror 150 so that the excitation light is reflected to the sample in the capillary tube 20 by the reflecting mirror 150 and the fluorescence generated from the sample is reflected to the fluorescence detecting part 170. Preferably, the motor 160 is a constant rotation motor for rotating the reflecting mirror 150 at a constant speed.

The fluorescence detecting part 170 functions to detect the fluorescence that is reflected by the reflecting mirror 150 and then passed through the beam splitter 120, thereby estimating the DNA amplification.

The fluorescence detecting part 170 may include a fluorescence condensing lens 171 for condensing the fluorescence passing through the beam splitter 120, a fluorescence band pass filter 172 for passing the condensed fluorescence having only a desired wavelength, and a fluorescence detecting sensor 173 for detecting the fluorescence having the desired wavelength passing through the fluorescence band pass filter 172. FIG. 5 shows a status of detecting the fluorescence having one wavelength.

As shown in FIG. 6, in order to detect the fluorescence having various kinds of wavelengths, the fluorescence detecting part 170 may further include one or more fluorescence condensing lenses 171, fluorescence band pass filters 172 and fluorescence beam splitters 174 according to a wavelength region of the fluorescence. At this time, the fluorescence beam splitters 174a and 174b are equipped differently from each other according to a wavelength of the fluorescence to be detected. The fluorescence condensing lenses 171a, 171b and 171c are equipped differently from each other according to a distance between the capillary tube 20 and the fluorescence detecting sensors 173a, 173b and 173c. The fluorescence band pass filters 172a, 172b and 172c are also equipped differently from each other according to a wavelength of the fluorescence to be detected.

Preferably, the fluorescence beam splitters 174a and 174b are the dichroic beam splitters by which a long wavelength is passed and a short wavelength is reflected on the basis of a desired wavelength. The desired wavelength is changed according to fluorescent dyes.

Figure 7:
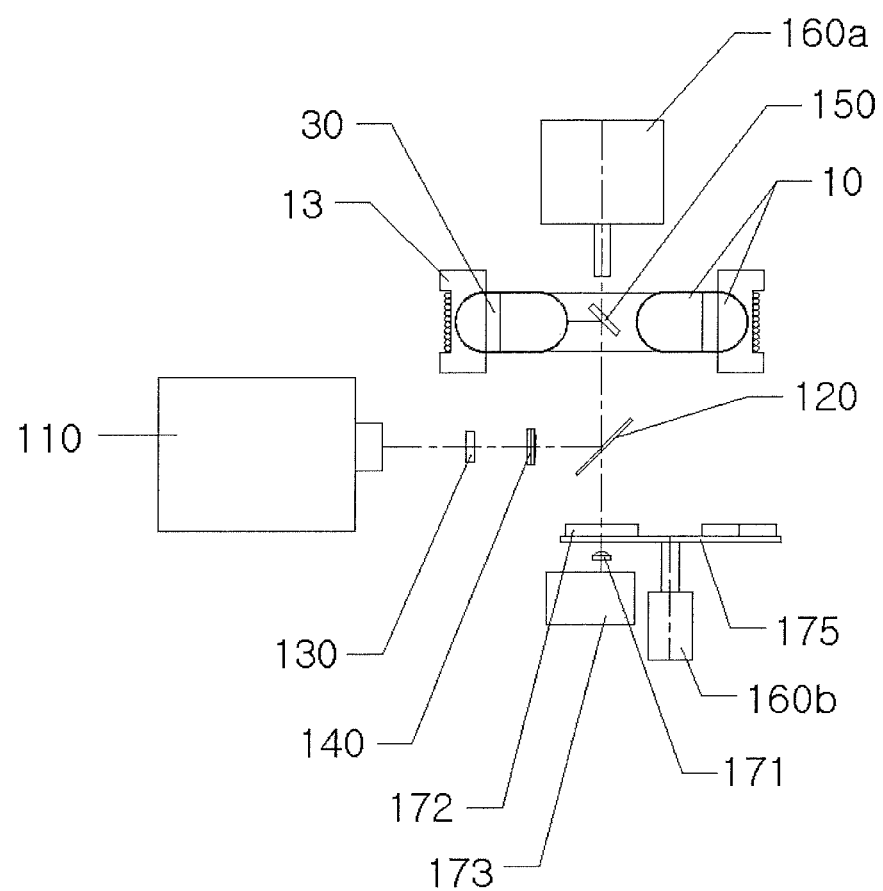
FIGS. 7 and 8 are schematic views showing the real-time monitoring apparatus using the thermal cycling reaction block in accordance with another embodiment of the present invention.
Figure 8:
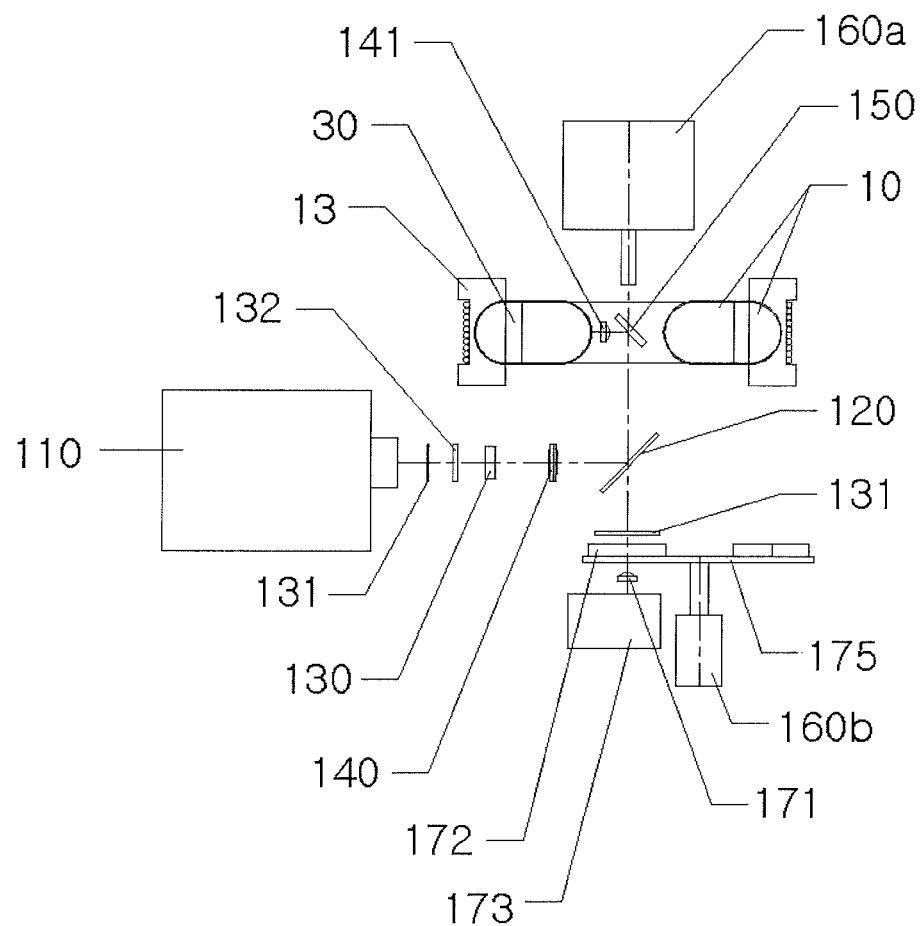

FIGS. 7 and 8 are schematic views showing the real-time monitoring apparatus using the thermal cycling reaction block in accordance with another embodiment of the present invention.

The real-time monitoring apparatus using the thermal cycling reaction block 100 in accordance with another embodiment of the present invention includes a light source 110 for irradiating excitation light; a band pass filter 130 for passing the excitation light having only a desired wavelength irradiated from the light source 110; a first condensing lens 140 for condensing the excitation light; a beam splitter 120 which reflects the excitation light and passes fluorescence generated from a sample in a capillary tube 20; a reflecting mirror 150 which is rotatably connected with a first motor 160a so as to transfer the excitation light reflected from the beam splitter 120 to the capillary tube 20 and reflect the fluorescence generated from the sample in the capillary tube 20; a second condensing lens 141 which is positioned between the reflecting mirror 150 and the thermal cycling reaction block 100 so as to condense the excitation light reflected from the reflecting mirror 150 and the fluorescence generated from a sample in a capillary tube 20; and a fluorescence detecting part 170 for detecting the fluorescence that is reflected by the reflecting mirror 150 and then passed through the beam splitter 120.

The light source 110 may include a white light source such as a tungsten halogen lamp and a xenon discharge lamp, and a single-colored light source such as LED and laser, but the light source 110 is not limited to them. In case that the light source 110 is laser, a neutral density (ND) filter 132 may be further provided to control an intensity of the laser.

Preferably, the second condensing lens 141 which is positioned between the reflecting mirror 150 and the thermal cycling reaction block 100 so as to condense the excitation light reflected from the reflecting mirror 150 and the fluorescence generated from a sample in a capillary tube 20 is an aspheric lens.

The fluorescence detecting part 170 may include a fluorescence condensing lens 171 for condensing the fluorescence passing through the beam splitter 120; a fluorescence band pass filter fixing part 175 which has one or more fluorescence band pass filters 172 for passing the fluorescence having different desired wavelengths from the condensed fluorescence; a second motor 160b for rotating the fluorescence band pass filter fixing part 175; and a fluorescence detecting sensor 173 for detecting the fluorescence having the desired wavelength passing through the fluorescence band pass filters 172.

The fluorescence detecting part 170 has one or more fluorescence band pass filters 172 provided on the fluorescence band pass filter fixing part 175. The fluorescence band pass filter fixing part 175 is connected with the second motor 160b to be rotated, so that the fluorescence is passed through each fluorescence band pass filter 172 provided on the fluorescence band pass filter fixing part 175 and then detected, thereby enhancing fluorescence detection and space efficiency.

In other words, as shown in FIG. 6, if multiple fluorescence band pass filters are used in the real-time monitoring apparatus, it is necessary to provide multiple fluorescence condensing lenses 171, fluorescence band pass filters 172 and fluorescence beam splitters 174 according to a (?) desired wavelength region of the fluorescence. However, as shown in FIGS. 7 and 8, since the real-time monitoring apparatus in accordance to another embodiment of the present invention has the multiple fluorescence band pass filters 172 provided on the fluorescence band pass filter fixing part 175, the fluorescence beam splitters 174 of FIG. 6 are not needed. Further, since only one fluorescence condensing lens 171 is needed, it is possible to reduce a manufacturing cost and a space occupation.

Preferably, the second motor 160b is a constant rotation motor for rotating the fluorescence band pass filter fixing part 175 including the fluorescence band pass filters 172 at a constant speed.

Preferably, the fluorescence detecting sensor 173 is a photo multiplier tube, and the fluorescence condensing lens 171 is an aspheric lens, but the fluorescence detecting sensor 173 and the fluorescence condensing lens 171 are not limited to them.

Further, in order to enhance an efficiency of separating the excitation light and the fluorescence, as shown in FIG.8, the real-time monitoring apparatus of the present invention may further include a polarizer or a polarizer film 131 between the light source 110 and the first condensing lens 140 and at the fluorescence measuring part.

While the present invention has been described with respect to the specific embodiments, it will be apparent to those skilled in the art that various changes and modifications may be made without departing from the spirit and scope of the invention as defined in the following claims.

[Industrial Applicability]

According to the present invention, since the real-time monitoring apparatus uses the fixed light source and fixed fluorescence detecting sensor so as to be fixed at a positioned controlled by rotation of the motor, it is facile to detect the amplification of the sample, and it is possible to enhance the detecting accuracy and reduce the manufacturing cost and effort, and it is also possible to reduce the malfunction and size thereof.

The invention claimed is:

1. A real-time monitoring apparatus comprising:
  a thermal cycling reaction block 100, comprising
    a doughnut-shaped first heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b; and
    a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction;
  a light source 110 for irradiating excitation light;
  a band pass filter 130 for passing the excitation light having only a desired wavelength irradiated from the light source 110;
  a first condensing lens 140 for condensing the excitation light;
  a beam splitter 120 which reflects the excitation light and passes fluorescence generated from a sample in a capillary tube 20;
  a reflecting mirror 150 which is rotatably connected with a motor 160 so as to transfer the excitation light reflected from the beam splitter 120 to the capillary tube 20 and reflect the fluorescence generated from the sample in the capillary tube 20, wherein the reflecting mirror 150 is disposed at the hollow part 11 formed at the central portion of the thermal cycling reaction block 100; and
  a fluorescence detecting part 170 for detecting the fluorescence that is reflected by the reflecting mirror 150 and then passes through the beam splitter 120.

2. The apparatus of claim 1, wherein the fluorescence detecting part 170 comprises:
  a fluorescence condensing lens 171 for condensing the fluorescence passing through the beam splitter 120;
  a fluorescence band pass filter 172 for passing only the condensed fluorescence having a desired wavelength; and
  a fluorescence detecting sensor 173 for detecting the fluorescence having the desired wavelength passing through the fluorescence band pass filter 172.

3. The apparatus of claim 2, wherein the fluorescence detecting part 170 further comprises one or more fluorescence condensing lenses 171, fluorescence band pass filters 172 and fluorescence beam splitters 174 according to a wavelength region of the fluorescence.

4. The apparatus of claim 1, wherein the motor 160 is a constant rotation motor for rotation at a constant speed.

5. A real-time monitoring apparatus comprising:
  a thermal cycling reaction block 100, comprising
  a doughnut-shaped first heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b;
  a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction; and
  a second heating block 13 located in contact with outer side of the doughnut-shaped first heating block 10,
  a light source 110 for irradiating excitation light;
  a band pass filter 130 for passing the excitation light having only a desired wavelength irradiated from the light source 110;
  a first condensing lens 140 for condensing the excitation light;
  a beam splitter 120 which reflects the excitation light and passes fluorescence generated from a sample in a capillary tube 20;
  a reflecting mirror 150 which is rotatably connected with a motor 160 so as to transfer the excitation light reflected from the beam splitter 120 to the capillary tube 20 and reflect the fluorescence generated from the sample in the capillary tube 20, wherein the reflecting mirror 150 is disposed at the hollow part 11 formed at the central portion of the thermal cycling reaction block 100; and a fluorescence detecting part 170 for detecting the fluorescence that is reflected by the reflecting mirror 150 and then passes through the beam splitter 120.

6. The apparatus of claim 5, wherein the fluorescence detecting part 170 comprises:

a fluorescence condensing lens 171 for condensing the fluorescence passing through the beam splitter 120;

a fluorescence band pass filter 172 for passing only the condensed fluorescence having a desired wavelength; and a fluorescence detecting sensor 173 for detecting the fluorescence having the desired wavelength passing through the fluorescence band pass filter 172.

7. The apparatus of claim 6, wherein the fluorescence detecting part 170 further comprises one or more fluorescence condensing lenses 171, fluorescence band pass filters 172 and fluorescence beam splitters 174 according to a wavelength region of the fluorescence.

8. The apparatus of claim 5, wherein the motor 160 is a constant rotation motor for rotation at a constant speed.

9. A real-time monitoring apparatus comprising:

a thermal cycling reaction block 100, a doughnut-shaped heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b; and a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction, wherein the doughnut-shaped heating block 10 is provided with a groove 12 on outer surface of the block 10 into which the capillary tube 20 is inserted;

a light source 110 for irradiating excitation light;

a band pass filter 130 for passing the excitation light having only a desired wavelength irradiated from the light source 110;

a first condensing lens 140 for condensing the excitation light;

a beam splitter 120 which reflects the excitation light and passes fluorescence generated from a sample in a capillary tube 20;

a reflecting mirror 150 which is rotatably connected with a motor 160 so as to transfer the excitation light reflected from the beam splitter 120 to the capillary tube 20 and reflect the fluorescence generated from the sample in the capillary tube 20, wherein the reflecting mirror 150 is disposed at the hollow part 11 formed at the central portion of the thermal cycling reaction block 100; and a fluorescence detecting part 170 for detecting the fluorescence that is reflected by the reflecting mirror 150 and then passes through the beam splitter 120.

10. The apparatus of claim 9, wherein the fluorescence detecting part 170 comprises:

a fluorescence condensing lens 171 for condensing the fluorescence passing through the beam splitter 120;

a fluorescence band pass filter 172 for passing only the condensed fluorescence having a desired wavelength; and a fluorescence detecting sensor 173 for detecting the fluorescence having the desired wavelength passing through the fluorescence band pass filter 172.

11. The apparatus of claim 10, wherein the fluorescence detecting part 170 further comprises one or more fluorescence condensing lenses 171, fluorescence band pass filters 172 and fluorescence beam splitters 174 according to a wavelength region of the fluorescence.

12. The apparatus of claim 9, wherein the motor 160 is a constant rotation motor for rotation at a constant speed.

13. The apparatus of claim 9, wherein the doughnut-shaped heating blocks 10a and 1b form a center hollow space, the center hollow space surrounded by the doughnut shaped heating blocks 10 and 10b and the reflecting mirror 150 is positioned in the center hollow space, and optionally wherein the light source is spaced from the center hollow space.

14. A real-time monitoring apparatus comprising:

a thermal cycling reaction block, comprising a doughnut-shaped first heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b;

a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction;

a light source 110 for irradiating excitation light;

a band pass filter 130 for passing only the excitation light having a desired wavelength irradiated from the light source 110;

a first condensing lens 140 for condensing the excitation light;

a beam splitter 120 which reflects the excitation light and passes fluorescence generated from a sample in a capillary tube 20;

a reflecting mirror 150 which is rotatably connected with a first motor 160a so as to transfer the excitation light reflected from the beam splitter 120 to the capillary tube 20 and reflect the fluorescence generated from the sample in the capillary tube 20, wherein the reflecting mirror 150 is disposed at the hollow part 11 formed at the central portion of the thermal cycling reaction block 100;

a second condensing lens 141 which is positioned between the reflecting minor 150 and the thermal cycling reaction block 100 so as to condense the excitation light reflected from the reflecting mirror 150 and the fluorescence generated from a sample in a capillary tube 20; and a fluorescence detecting part 170 for detecting the fluorescence that is reflected by the reflecting mirror 150 and then passes through the beam splitter 120.

15. The apparatus of claim 14, wherein the fluorescence detecting part 170 comprises:
- a fluorescence condensing lens 171 for condensing the fluorescence passing through the beam splitter 120;
- a fluorescence band pass filter fixing part 175 which has one or more fluorescence band pass filters 172 for passing the fluorescence having different desired wavelengths from the condensed fluorescence;
- a second motor 160b for rotating the fluorescence band pass filter fixing part 175; and
- a fluorescence detecting sensor 173 for detecting the fluorescence having the desired wavelength passing through the fluorescence band pass filters 172.

16. The apparatus of claim 14, further comprising a polarizer or a polarizer film 131 between the light source 110 and the condensing lens 140 and at a fluorescence measuring part.

17. The apparatus of claim 15, wherein the first motor 160a and the second motor 160b are constant rotation motors for rotation at a constant speed.

18. A real-time monitoring apparatus comprising:
a thermal cycling reaction block, comprising
- a doughnut-shaped first heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b;
- a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction; and
- a second heating block 13 located in contact with outer side of the doughnut-shaped first heating block 10,
a light source 110 for irradiating excitation light;
a band pass filter 130 for passing only the excitation light having a desired wavelength irradiated from the light source 110;
a first condensing lens 140 for condensing the excitation light;
a beam splitter 120 which reflects the excitation light and passes fluorescence generated from a sample in a capillary tube 20;
a reflecting mirror 150 which is rotatably connected with a first motor 160a so as to transfer the excitation light reflected from the beam splitter 120 to the capillary tube 20 and reflect the fluorescence generated from the sample in the capillary tube 20;
a second condensing lens 141 which is positioned between the reflecting minor 150 and the thermal cycling reaction block 100 so as to condense the excitation light reflected from the reflecting mirror 150 and the fluorescence generated from a sample in a capillary tube 20, wherein the reflecting minor 150 is disposed at the hollow part 11 formed at the central portion of the thermal cycling reaction block 100; and
a fluorescence detecting part 170 for detecting the fluorescence that is reflected by the reflecting mirror 150 and then passes through the beam splitter 120.

19. The apparatus of claim 18, wherein the fluorescence detecting part 170 comprises:
- a fluorescence condensing lens 171 for condensing the fluorescence passing through the beam splitter 120;
- a fluorescence band pass filter fixing part 175 which has one or more fluorescence band pass filters 172 for passing the fluorescence having different desired wavelengths from the condensed fluorescence;
- a second motor 160b for rotating the fluorescence band pass filter fixing part 175; and
- a fluorescence detecting sensor 173 for detecting the fluorescence having the desired wavelength passing through the fluorescence band pass filters 172.

20. The apparatus of claim 18, further comprising a polarizer or a polarizer film 131 between the light source 110 and the condensing lens 140 and at a fluorescence measuring part.

21. The apparatus of claim 19, wherein the first motor 160a and the second motor 160b are constant rotation motors for rotation at a constant speed.

22. A real-time monitoring apparatus comprising:
a thermal cycling reaction block, comprising
- a doughnut-shaped heating block 10, said doughnut-shaped heating block comprising a region 10a, a region 10b, and an insulating layer 30 which is placed between the region 10a and the region 10b so as to separate the region 10a from the region 10b, wherein said region 10a, insulating layer 30, and region 10b are circular around a common axis at the center of the doughnut-shaped heating block 10 and wherein a temperature of the region 10a is different from a temperature of the region 10b; and
- a capillary tube 20 wound around the doughnut-shaped heating block 10 through a hollow part 11 of the doughnut-shaped heating block 10 at a regular interval to as to a respective individual turn of the wounded capillary tube 20 be in contact with surfaces of the region 10a, insulation layer 30, region 10b, insulation layer 30, and region 10a in this order, wherein the capillary tube 20 has an inlet to receive a sample to be subjected to a thermal cycling reaction and an outlet to output the sample after the thermal cycling reaction,
wherein the doughnut-shaped heating block 10 is provided with a groove 12 on outer surface of the block 10 into which the capillary tube 20 is inserted;
a light source 110 for irradiating excitation light;
a band pass filter 130 for passing only the excitation light having a desired wavelength irradiated from the light source 110;
a first condensing lens 140 for condensing the excitation light;
a beam splitter 120 which reflects the excitation light and passes fluorescence generated from a sample in a capillary tube 20;
a reflecting mirror 150 which is rotatably connected with a first motor 160a so as to transfer the excitation light reflected from the beam splitter 120 to the capillary tube 20 and reflect the fluorescence generated from the sample in the capillary tube 20;
a second condensing lens 141 which is positioned between the reflecting minor 150 and the thermal cycling reaction block 100 so as to condense the excitation light reflected from the reflecting mirror 150 and the fluorescence generated from a sample in a capillary tube 20, wherein the reflecting minor 150 is disposed at the hollow part 11 formed at the central portion of the thermal cycling reaction block 100; and a fluorescence detecting part 170 for detecting the fluorescence that is reflected by the reflecting mirror 150 and then passes through the beam splitter 120.

23. The apparatus of claim 22, wherein the fluorescence detecting part 170 comprises:

a fluorescence condensing lens 171 for condensing the fluorescence passing through the beam splitter 120;

a fluorescence band pass filter fixing part 175 which has one or more fluorescence band pass filters 172 for passing the fluorescence having different desired wavelengths from the condensed fluorescence;

a second motor 160*b* for rotating the fluorescence band pass filter fixing part 175; and a fluorescence detecting sensor 173 for detecting the fluorescence having the desired wavelength passing through the fluorescence band pass filters 172.

24. The apparatus of claim 22, further comprising a polarizer or a polarizer film 131 between the light source 110 and the condensing lens 140 and at a fluorescence measuring part.

25. The apparatus of claim 23, wherein the first motor 160*a* and the second motor 160*b* are constant rotation motors for rotation at a constant speed.

* * * * *